United States Patent
Osorio

(10) Patent No.: US 9,579,508 B2
(45) Date of Patent: Feb. 28, 2017

(54) SELECTIVE RECRUITMENT AND ACTIVATION OF FIBER TYPES IN NERVES FOR THE CONTROL OF UNDESIRABLE BRAIN STATE CHANGES

(71) Applicant: Ivan Osorio, Leawood, KS (US)

(72) Inventor: Ivan Osorio, Leawood, KS (US)

(73) Assignee: Ivan Osorio, Leawood, KS (US)

(*) Notice: Subject to any disclaimer, the term of this patent is extended or adjusted under 35 U.S.C. 154(b) by 0 days.

(21) Appl. No.: 14/530,964

(22) Filed: Nov. 3, 2014

(65) Prior Publication Data
US 2015/0051637 A1 Feb. 19, 2015

Related U.S. Application Data

(63) Continuation of application No. 13/765,795, filed on Feb. 13, 2013, now Pat. No. 8,880,167.

(51) Int. Cl.
| | | |
|---|---|---|
| A61N 1/36 | (2006.01) | |
| A61N 1/05 | (2006.01) | |
| A61H 9/00 | (2006.01) | |
| A61B 17/12 | (2006.01) | |
| A61F 7/12 | (2006.01) | |
| A61H 39/08 | (2006.01) | |

(52) U.S. Cl.
CPC .......... *A61N 1/36146* (2013.01); *A61B 17/12* (2013.01); *A61F 7/12* (2013.01); *A61H 9/0092* (2013.01); *A61H 39/08* (2013.01); *A61N 1/0556* (2013.01); *A61N 1/36053* (2013.01); *A61N 1/36064* (2013.01); *A61N 1/36082* (2013.01); *A61N 1/36096* (2013.01); *A61H 2201/0207* (2013.01); *A61H 2201/0214* (2013.01); *A61H 2201/0242* (2013.01); *A61H 2201/0285* (2013.01); *A61H 2201/5005* (2013.01); *A61H 2205/027* (2013.01); *A61H 2230/045* (2013.01); *A61H 2230/065* (2013.01); *A61H 2230/405* (2013.01); *A61H 2230/425* (2013.01); *A61H 2230/605* (2013.01); *A61H 2230/655* (2013.01)

(58) Field of Classification Search
CPC .. A61N 1/0531; A61N 1/0551; A61N 1/0556; A61N 1/36025; A61N 1/36053; A61N 1/36064; A61N 1/36082; A61N 1/36096; A61N 1/36114; A61N 1/36146; A61B 17/12
USPC ................................ 607/3, 45, 116, 117, 118
See application file for complete search history.

(56) References Cited

U.S. PATENT DOCUMENTS

| | | | | |
|---|---|---|---|---|
| 5,203,326 A | * | 4/1993 | Collins | .............. A61N 1/36114 607/4 |
| 5,288,723 A | * | 2/1994 | Strichartz | ............. A61K 31/445 454/10 |

(Continued)

*Primary Examiner* — Christopher A Flory
(74) *Attorney, Agent, or Firm* — Rodney J. Fuller; Booth Udall Fuller, PLC

(57) ABSTRACT

We disclose methods and medical device systems for selectively recruiting a nerve fiber type within a cranial nerve, a peripheral nerve or a spinal root. Such a method may comprise applying a first pressure, a heating, and/or a cooling to a second location of the nerve, the pressure, heating, or cooling sufficient to substantially block at least one of activation or conduction in at least one fiber population through the second location of the nerve for a blocking time period; and applying an electrical signal to a first location during the blocking time period.

11 Claims, 7 Drawing Sheets

(56) References Cited

U.S. PATENT DOCUMENTS

| | | | | |
|---|---|---|---|---|
| 5,755,750 A * | 5/1998 | Petruska | A61N 1/0551 | 607/118 |
| 6,341,236 B1 * | 1/2002 | Osorio | A61N 1/36053 | 607/45 |
| 6,761,715 B2 * | 7/2004 | Carroll | A61B 18/02 | 128/898 |
| 7,162,303 B2 * | 1/2007 | Levin | A61M 5/14276 | 607/44 |
| 7,300,449 B2 * | 11/2007 | Mische | A61N 1/36082 | 606/198 |
| 7,444,184 B2 * | 10/2008 | Boveja | A61N 1/36014 | 607/118 |
| 7,529,582 B1 * | 5/2009 | DiLorenzo | A61N 1/36007 | 607/2 |
| 7,599,736 B2 * | 10/2009 | DiLorenzo | A61N 1/36007 | 607/2 |
| 7,890,185 B2 * | 2/2011 | Cohen | A61N 1/36007 | 607/118 |
| 7,937,145 B2 * | 5/2011 | Dobak | A61B 5/4872 | 607/2 |
| 8,150,518 B2 * | 4/2012 | Levin | A61M 5/14276 | 607/118 |
| 8,180,446 B2 * | 5/2012 | Dacey, Jr. | A61B 5/04001 | 607/2 |
| 8,560,073 B2 * | 10/2013 | Osorio | A61B 5/0476 | 600/378 |
| 8,562,524 B2 * | 10/2013 | Osorio | A61B 5/7275 | 600/300 |
| 8,571,653 B2 * | 10/2013 | Ben-David | A61N 1/36071 | 607/2 |
| 8,600,511 B2 * | 12/2013 | Yared | A61B 5/0031 | 607/44 |
| 8,734,499 B2 * | 5/2014 | Lovett | A61F 7/12 | 607/105 |
| 8,880,167 B2 * | 11/2014 | Osorio | A61N 1/36053 | 607/116 |
| 2002/0161360 A1 * | 10/2002 | Carroll | A61B 18/02 | 606/21 |
| 2004/0082984 A1 * | 4/2004 | Osorio | A61F 7/12 | 607/105 |
| 2009/0149693 A1 * | 6/2009 | Dacey, Jr. | A61B 5/04001 | 600/9 |
| 2009/0149694 A1 * | 6/2009 | Dacey, Jr. | A61B 5/04001 | 600/9 |
| 2009/0149797 A1 * | 6/2009 | Dacey, Jr. | A61B 5/4041 | 604/20 |
| 2009/0149798 A1 * | 6/2009 | Dacey, Jr. | A61B 5/4041 | 604/20 |
| 2009/0149895 A1 * | 6/2009 | Dacey, Jr. | A61B 5/04001 | 607/3 |
| 2009/0149896 A1 * | 6/2009 | Dacey, Jr. | A61B 5/4041 | 607/3 |
| 2009/0149911 A1 * | 6/2009 | Dacey, Jr. | A61N 1/36014 | 607/45 |
| 2009/0149912 A1 * | 6/2009 | Dacey, Jr. | A61N 1/0556 | 607/45 |
| 2009/0149919 A1 * | 6/2009 | Dacey, Jr. | A61B 5/411 | 607/62 |
| 2009/0149926 A1 * | 6/2009 | Dacey, Jr. | A61B 5/411 | 607/96 |
| 2011/0160795 A1 * | 6/2011 | Osorio | A61B 5/0476 | 607/45 |
| 2012/0022409 A1 * | 1/2012 | Gertner | A61B 19/5225 | 601/2 |
| 2012/0029591 A1 * | 2/2012 | Simon | A61N 1/40 | 607/42 |
| 2012/0172652 A1 * | 7/2012 | Dacey, Jr. | A61N 1/36135 | 600/9 |
| 2012/0172680 A1 * | 7/2012 | Gelfand | A61N 1/365 | 600/301 |
| 2012/0215218 A1 * | 8/2012 | Lipani | A61B 18/1492 | 606/41 |
| 2012/0265262 A1 * | 10/2012 | Osorio | A61B 5/0476 | 607/3 |
| 2012/0298105 A1 * | 11/2012 | Osorio | A61N 1/0546 | 128/203.14 |
| 2013/0138193 A1 * | 5/2013 | Durand | A61N 1/36071 | 607/118 |
| 2013/0178910 A1 * | 7/2013 | Azamian | A61B 17/00234 | 607/33 |
| 2013/0310823 A1 * | 11/2013 | Gelfand | A61B 18/1492 | 606/33 |
| 2013/0324989 A1 * | 12/2013 | Leung | A61B 18/02 | 606/24 |
| 2014/0066923 A1 * | 3/2014 | Azamian | A61B 17/00234 | 606/33 |
| 2014/0135876 A1 * | 5/2014 | Lipani | A61B 18/1492 | 607/99 |
| 2014/0163647 A1 * | 6/2014 | Dacey, Jr. | A61M 37/00 | 607/60 |
| 2014/0186341 A1 * | 7/2014 | Mayse | A61B 18/18 | 424/133.1 |
| 2014/0228900 A1 * | 8/2014 | Osorio | A61N 1/36053 | 607/3 |
| 2014/0257263 A1 * | 9/2014 | Azamian | A61B 17/00234 | 606/28 |
| 2014/0276353 A1 * | 9/2014 | Osorio | A61B 17/1325 | 604/20 |
| 2014/0276549 A1 * | 9/2014 | Osorio | A61M 5/1723 | 604/503 |
| 2015/0005680 A1 * | 1/2015 | Lipani | A61B 18/1492 | 601/15 |
| 2015/0011989 A1 * | 1/2015 | Azamian | A61B 17/00234 | 606/33 |
| 2015/0045675 A1 * | 2/2015 | Chernomorsky | A61M 29/02 | 600/471 |
| 2015/0051594 A1 * | 2/2015 | Sobotka | A61N 1/36057 | 606/21 |
| 2015/0224301 A1 * | 8/2015 | Durand | A61N 1/36071 | 607/118 |
| 2016/0074661 A1 * | 3/2016 | Lipani | A61B 18/1492 | 601/18 |

* cited by examiner

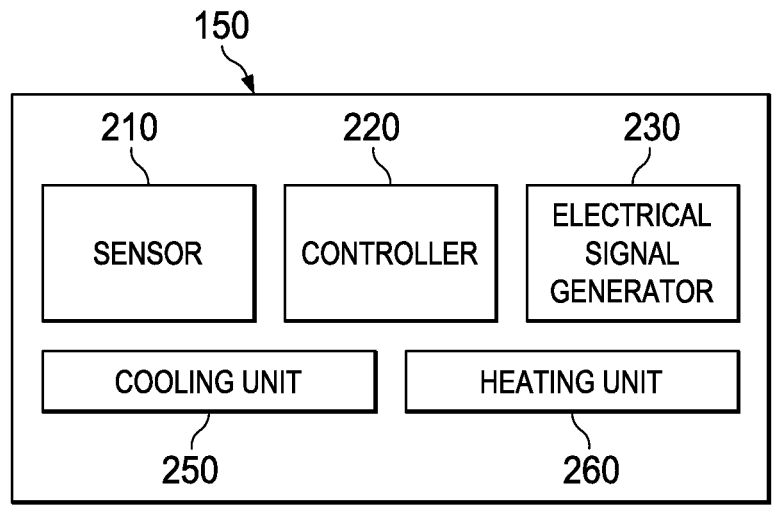
FIG. 2B
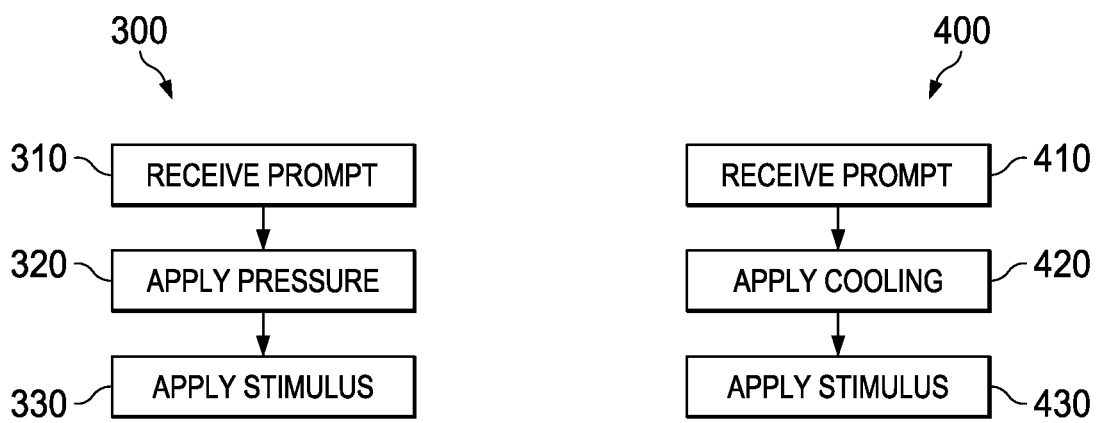
FIG. 3
FIG. 4

SELECTIVE RECRUITMENT AND ACTIVATION OF FIBER TYPES IN NERVES FOR THE CONTROL OF UNDESIRABLE BRAIN STATE CHANGES

PRIORITY STATEMENT

This application is a continuation application of U.S. patent application Ser. No. 13/765,795, filed Feb. 13, 2013 and issued as U.S. Pat. No. 8,880,167 on Nov. 4, 2014. U.S. patent application Ser. No. 13/765,795 is hereby incorporated herein by reference in its entirety.

FIELD OF THE INVENTION

This invention relates to medical device systems and methods capable of selective recruitment, activation and/or conduction of fiber types in nerves, such as cranial or, peripheral, and spinal roots.

DESCRIPTION OF THE RELATED ART

Therapies using electrical signals to provide a therapy to a patient (electro-therapy) are beneficial for certain neurological disorders, such as epilepsy and depression. Implantable medical devices (IMDs) have been effectively used to deliver therapeutic electrical stimulation to various portions of the human body (e.g., the vagus nerve) for treating epilepsy. As used herein, "stimulation," "neurostimulation," "stimulation signal," "therapeutic signal," or "neurostimulation signal" refers to the direct or indirect application of an electrical, mechanical, thermal, magnetic, electro-magnetic, photonic, acoustic, cognitive, and/or chemical signal to an organ or a neural structure in the patient's body. The stimulation signal is an exogenous signal distinct from the endogenous electro-chemical or thermal activity inherent to the patient's body. In other words, the therapeutic stimulation signal (whether electrical, mechanical, thermal, magnetic, electro-magnetic, photonic, acoustic, cognitive, and/or chemical in nature) applied to a cranial nerve or to other nervous tissue structure in the present disclosure is a signal applied from a medical device, e.g., a neurostimulator.

When a neurostimulation signal (whether of an electrical, mechanical, thermal, or other modality) is applied to a neural structure, energy from the signal enters nerve fibers within the structure. If the energy from the signal exceeds a threshold, the signal will cause the nerve fiber to generate an action potential that may be transmitted along the length of the nerve. Stimulation of a nerve fiber in an amount sufficient to generate an action potential is referred to herein as "recruitment" of the nerve fiber. The effect of the recruiting stimulation signal that (i.e., generation of an action potential in the fiber) is termed "activation." Depending upon the amount of energy it contains, the signal may recruit none, some, or nearly all of the fibers types within a neural structure.

Although neurostimulation has proven effective in the treatment of a number of medical conditions, it would be desirable to further enhance and optimize neurostimulation-based therapies to neural structures. For example, nerves (such as cranial nerves) typically possess multiple types of fibers, such as myelinated (e.g., A- and B-fibers) and unmyelinated (e.g., C-fibers) with different conduction velocities that are a function not only of the presence or absence of a myelin sheath but also of the fibers' diameter. In general, larger diameter fibers conduct nervous impulses faster than those with smaller diameters, and impulses travel faster in myelinated (i.e. insulated) than in unmyelinated (non-insulated) fibers.

There may be situations in which selective recruitment and/or activation of a particular fiber type or types would lead to greater efficacy or to other benefits such as reduction in the frequency or severity of adverse or deleterious effects, of a neurostimulation-based therapy. However, in the current state of the art, selective recruitment of fiber types is performed by adjusting the amplitude of a therapeutic electrical signal, a highly limiting approach since it does not lend to selective recruitment and/or activation of small diameter nerve fibers. Because the activation thresholds (AT) of fiber types A, B, and C can be quantitatively ordered as $ATA<ATB<ATc$, it is possible to administer an electrical signal having an amplitude greater than ATA but less than ATB to selectively recruit A-fibers. Similarly, an electrical signal having an amplitude greater than ATB but less than ATC would selectively recruit A- and B-fibers. However, to recruit B-fibers, A-fibers must also be activated, and to recruit C-fibers, both A- and B-fibers must also be activated when electrical currents are delivered to the whole of a nerve trunk. Also, if only A-fibers are desired to be recruited, an electrical current having an amplitude greater than ATB would also activate B-fibers.

Therefore, it would be desirable to have alternative techniques for selective activation of fiber types in nerves.

SUMMARY OF THE INVENTION

In some embodiments, the present disclosure relates to a method for selectively recruiting a nerve fiber type within a cranial nerve, a peripheral nerve or a spinal root, comprising applying a first pressure to a second location of said nerve, said pressure sufficient to substantially block at least one of activation or conduction in at least one of an A-fiber population or a B-fiber population through said second location of said nerve for a blocking time period; and applying an electrical signal to a first location during said blocking time period.

In some embodiments, the present disclosure relates to a method for selectively recruiting a nerve fiber type of a nerve, comprising performing an operation selected from one of heating or cooling a second location of said nerve, said heating or cooling sufficient to substantially block at least one of activation or conduction on at least a first fiber type of said nerve for a blocking time period; and applying said electrical signal to said first location during said blocking time period.

In some embodiments, the present disclosure relates to a medical device system for selectively stimulating a nerve fiber, comprising an electrode coupled to a first location of a nerve, said electrode capable of applying an electrical signal to said first location; a nerve pressure device coupled to a second location of said nerve, capable of applying a first pressure to the second location; a medical device operatively coupled to said electrode and said nerve pressure device, said medical device comprising a controller; an electrical signal generator to apply an electrical signal to the first location of said nerve using said electrode; and a pressure signal generator to apply said first pressure to said second location of said nerve using said nerve pressure device, to substantially block at least one of activation or conduction in at least one of an A-fiber population or a B-fiber population at said second location of said nerve.

BRIEF DESCRIPTION OF THE DRAWINGS

The invention may be understood by reference to the following description taken in conjunction with the accompanying drawings, in which like reference numerals identify like elements, and in which:

FIG. 2B provides a block diagram of a medical device, in accordance with one illustrative embodiment of the present disclosure;

FIG. 3 provides a flowchart of a method for selectively recruiting and/or activating a fiber type, in accordance with one illustrative embodiment of the present disclosure;

FIG. 4 provides a flowchart of another method of selectively recruiting and/or activating a fiber type, in accordance with one illustrative embodiment of the present disclosure;

Figure 1A:
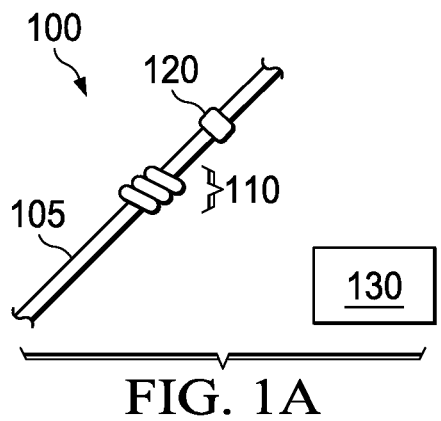
FIG. 1A provides a stylized diagram of a medical device system implanted into a patient's body, in accordance with one illustrative embodiment of the present disclosure.

While the disclosure is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the disclosure are described herein. For clarity, not all features of an actual implementation are described. In the development of any actual embodiment, numerous implementation-specific decisions must be made to achieve design-specific goals, which will vary from one implementation to another. Such a development effort, while possibly complex and time-consuming, would nevertheless be a routine undertaking for persons of ordinary skill in the art having the benefit of this disclosure.

This document does not intend to distinguish between components that differ in name but not function. In the discussion and claims, the terms "including" and "includes" are used in an open-ended fashion, and should be interpreted to mean "including, but not limited to." The term "couple" or "couples" is intended to mean either a direct or an indirect electrical connection. "Direct contact," "direct attachment," or providing a "direct coupling" indicates that a surface of a first element contacts the surface of a second element with no substantial attenuating medium there between. The presence of small quantities of substances, such as bodily fluids, that do not substantially attenuate electrical connections does not vitiate direct contact. The word "or" is used in the inclusive sense (i.e., "and/or") unless a specific use to the contrary is explicitly stated.

The term "electrode" or "electrodes" described herein may refer to one or more stimulation electrodes (i.e., electrodes for delivering a therapeutic signal generated by an IMD to a tissue), sensing electrodes (i.e., electrodes for sensing a physiological indication of a state of a patient's body), and/or electrodes that are capable of delivering a therapeutic signal, as well as performing a sensing function.

Embodiments of the present disclosure provide improved therapies for treating medical conditions by selective recruitment of different types of nerve fibers. As previously noted, different types of nerve fibers (e.g., the A, B, and C major fiber types, including their various sub-types such as A$\alpha$, A$\beta$, A$\gamma$, A$\delta$) have different activation and/or conduction thresholds for induction of action potentials therein and/or for allowing continued conduction of action potentials along the fiber. A principal difficulty in prior attempts to provide "fiber-type specific" neural stimulation (including particularly electrical neurostimulation) is the difficulty of selectively recruiting fibers having a higher activation or conduction threshold (e.g., C fibers) without also recruiting fibers having a lower activation threshold (e.g., A and B fibers and sub-types thereof). The nerve fiber classification/nomenclature used in this disclosure was proposed by Erlanger and Gasser; there is also a numerical classification [Ia (A$\alpha$), Ib (A$\alpha$), II (A$\beta$), III (A$\delta$), IV (C fibers)] that is listed here in the spirit of full disclosure.

Selective activation of nerve fibers may have different effects on a target structure (e.g., brain nuclei or cortex) from those obtained when the entire nerve trunk (and thus all fiber types) are activated. For example, activation of large myelinated fibers has a different effect upon cortical rhythms than activation of small fibers. This difference may be exploited, for example, in treating diseases associated with or caused by disturbed/abnormal cortical rhythms, such as epilepsy or when blockage of conduction of nerve impulses along certain fiber types is warranted such as in the treatment of pain.

Recruitment of fiber types in a cranial or peripheral nerve or in a spinal root, may be also accomplished through the placement of small electrodes inside the nerve (i.e., beneath the epineurium or intra-fascicularly) and in close proximity to the targeted fiber-type bundle(s). This is possible given the histologic organization of fiber types in bundles or "clusters". Localization of bundles may be performed using one or more of: a) high resolution electrode arrays and spatio-temporal analyses of evoked nerve activity using electro-physiological tools (e.g., neurogram) and, when necessary, statistical/mathematical methods, b) static and/or functional imaging such as that made possible by certain MR modalities, near-infra red spectroscopy, etc., or c) the patient's perception of sensations elicited by stimulation (or micro-stimulation) of fiber bundles. For example, if the patient reports a sensation of discomfort or pain, it may be deduced that very thinly myelinated or unmyelinated small diameter fibers are being activated by said stimulation.

The present disclosure provides methods and devices that temporarily alter the activation and/or conduction threshold (s) of one of more fiber types relative to other fiber types. This may facilitate selective recruitment of particular fiber types by blocking electrical conduction on particular fibers through a first location of a nerve and/or action potential activation of particular fibers at a second location of the nerve. In one embodiment, the thresholds of fibers having lower activation/conduction thresholds is temporarily increased relative to the threshold of fibers with higher thresholds. This may be done by stimulating the lower-threshold fibers (e.g., A fibers) with a different mode or type of stimulation to temporarily alter (e.g., raise) the threshold of the lower-threshold fibers relative to the naturally higher threshold fibers. For example, the activation/conduction threshold for a first fiber type and a first stimulation modality (e.g., the threshold for A fibers with an electrical stimulation) may be temporarily altered relative to that of a second fiber (e.g., the threshold of C fibers with an electrical stimulation) by providing a second stimulation modality (e.g., a mechanical stimulation such as pressure) to a neural structure having both the low-threshold and high-threshold fiber types. The activation threshold for the low-threshold fibers (e.g., A fibers) may be temporarily increased relative to the high-threshold fibers (e.g., C fibers) such that when the first stimulation modality (e.g., electrical stimulation) is provided to the neural structure in close temporal proximity (e.g., simultaneously or during a refractory period) to the second stimulation modality, the higher-threshold fibers may be preferentially or selectively recruited relative to the lower-threshold fibers.

In this disclosure a distinction is made between fiber activation and conduction of an action potential. That is, a fiber may be activated in that an action potential is generated in the vicinity of the stimulus site, but not conducted/propagated beyond it, due to blockage of a segment or segment(s) of the activated fiber.

Selective recruitment or activation of nerve fibers may be performed in one of two ways: 1. activation of only certain fiber types, and 2. activation of all fiber types in a nerve trunk, and blockage of conduction along certain fibers. The first case (activating only certain fiber types) may occur when low amplitude, high frequency electrical currents are delivered to a nerve trunk containing A, B and C fiber types. In this case to the bio-physical properties of the fibers, only or mainly A fibers are activated. However, given the inherent differences in action potential thresholds among fiber types, (C fibers threshold>B fibers threshold>A fibers threshold), it is not usually possible using electrical currents to activate C fibers without co-activating B and A fibers. In this case, selective recruitment/activation of fibers is accomplished via blockage of propagation of action potentials along certain fiber types. For example, selective recruitment of C-fibers is performed through activation of all fiber types (A, B & C) within a nerve, and blockage of conduction via cooling of or pressure on the nerve of A & B fibers.

As used herein, "selective recruitment" and "preferential recruitment" refer to increasing the fraction of higher-threshold fibers that are activated (e.g., by creating an action potential therein) and/or decreasing the fraction of lower-threshold fibers that are activated, by a first stimulation modality such as an electrical signal applied to the neural structure. In one embodiment, the term selective recruitment is applied to the nerve fiber type having the higher innate or native (i.e., unaltered) activation/conduction threshold (e.g. C fibers). The term "modify conduction" refers to one or more of dampening, attenuating, slowing, reducing or blocking impulse conduction (e.g., the induction and movement of an action potential) on a nerve fiber type. In one embodiment, "modify conduction" is applied to the fiber type having the lower native threshold (e.g., A fibers), and whose threshold is raised by the second stimulation modality (e.g., increased positive pressure). It will be appreciated, however, that the terms are related, and together refer to the effects of first and second stimulation modalities applied to a nerve structure having two or more of low-threshold (A), intermediate (B) and high-threshold (C) fibers therein. The terms do not imply that no fibers of the low-threshold type (i.e., the fibers whose threshold is temporarily altered or whose conduction is modified) are recruited or activated, although in some embodiments action potentials may be generated only in the high-threshold fibers. Instead, "selective recruitment" and/or "modified conduction" may together involve recruiting a higher fraction of the high-threshold fibers relative to the low-threshold fibers than would be the case if only the first stimulation modality were applied without the second stimulation modality. In the example previously discussed, a higher fraction of C fibers in a nerve structure may be activated by electrical stimulation (relative to the fraction of A fibers and/or B fibers) when the electrical stimulation signal is provided in close temporal proximity to mechanical stimulation of the nerve structure—either while the mechanical stimulation is being provided, or during a refractory period shortly thereafter in which the threshold(s) of the A and/or B fibers remain elevated relative to their thresholds without the presence of the second stimulation modality.

As previously noted, selective recruitment of particular types of nerve fibers may be used to provide enhanced or different effects on one or more end-target structures (e.g., brain nuclei or cortex) from those obtained when the entire nerve structure (and thus all fiber types) is stimulated using only a single stimulation modality (e.g., only electrical stimulation). Where only one type of stimulation modality is employed, fibers are recruited according to their unaltered thresholds, and thus effects attributable to the action of higher-threshold fibers (e.g., C-fibers) in end-target structures such as brain nuclei may be undesirably small or reflect the "mixture" of action potentials with different conduction velocities and amplitudes traveling along the various fiber types leading to spatio-temporal dispersion. Conversely, undesired effects attributable to lower-threshold fibers may be undesirably large. Embodiments of the present disclosure may be employed to provide improved therapeutic outcomes and/or minimized adverse side effects.

Several stimulation modalities applied alone or in any possible combination, temporal sequence and parameters (e.g., intensity, duration of stimulation, waveform, rate of delivery, etc.) may be used for selectively recruiting fiber types in a cranial nerve, a peripheral nerve or a spinal root, including: 1. mechanical stimulation (e.g., changes in pressure in reference to that normally acting on the body); 2. thermal stimulation (e.g., changes in temperature in reference to normal body temperature); 3. electrical stimulation, either as alternating or direct current and at either high frequencies (defined herein as at no less than 1 KHz) or low frequencies (defined herein as no greater than 100 Hz) of adequate pulse width, pulse shape, intensity and duration; 4. chemical stimulation (e.g., local anesthetics such as lidocaine; ions such as Ca++, Mg++ or KC1, etc.); 5. application of stimuli to skin, muscle or tendon receptors capable of naturally activating specific fiber types; for example noxious stimuli such as heat or pinprick may be delivered to the ears' conchae to activate very thinly myelinated or unmyelinated (e.g., C fibers) small diameter vagal fibers.

Other strategies (e.g., exploitation of anatomo-histological properties) may be employed to selectively activate certain fibers types: abdominal vagi nerves are composed almost entirely of unmyelinated fibers. Stimulation of these segments of the vagus may be performed whenever the clinical case calls for selective activation of C fibers. The superior laryngeal branch of the vagus nerve, contains 70% of unmyelinated fibers. Stimulation of this nerve using, for example, intra-fascicular electrodes would increase the probability of selective activation of C fibers, given they occupy most of the cross section of this branch.

In a particular example, application of sufficient pressure to a first location on a nerve structure (e.g., a cervical portion of a vagus nerve) having A-, B-, and C-fibers may reduce the ability of A-fibers (or both A- and B-fibers) to conduct action potentials, and/or raise the threshold necessary for an electrical signal to induce action potentials in A and/or B-fibers, at the first location. Therefore, if an electrical signal is applied to a second location on the nerve structure, wherein the electrical currents would—absent the pressure applied to the first location—elicit action potentials in A-, B-, and C-fibers, conduction of such action potentials on the A-fibers or the A- and B-fibers may be blocked at the second location, while conduction of such action potentials on B- and C-fibers or C-fibers alone, may proceed through the second location. In other words, the medical device system 100 may be used to selectively recruit C-fibers or B- and C-fibers in the nerve.

The amount of pressure sufficient to block action potential conduction of A-fibers, A- and B-fibers, or A-, B-, and C-fibers may be determined as a routine matter by persons of skill in the art having the benefit of the present disclosure. For example, the amount of pressure may be determined by recording a neurogram relating to conduction through the second location of the nerve; and determining a first pressure threshold required to block or substantially reduce conduction along at least one of an A fiber population or a B fiber population(s) based upon the neurogram. The pressure (or temperature, chemical or other stimulation modality) changes required to recruit a certain fiber type, may be also determined based on the effect on the organism of stimulation of the nerve. Simultaneous recording of the action potentials triggered by stimulation and of other body signals (e.g. EKG, ECoG, voice properties/quality/vocal cord contractions, gastrogram, etc.) allows correlation of the change in body signal with fiber group activity; attenuation or disappearance of changes in a body signal correlated with activation of a certain fiber type, is indicative of blocked conduction along said fibers.

In certain embodiments of this disclosure, alteration of electrical activation and/or electrical conduction thresholds may be accomplished by applying mechanical, thermal or chemical stimulation. More generally, a second stimulation modality may be used to alter one or more of activation or conduction thresholds associated with a first stimulation modality, where the first and second modalities of stimulation are selected from electrical, mechanical, thermal, chemical, magnetic, and optical stimulation modalities.

In another embodiment, A and/or B type fibers may be selectively recruited and activated by either exploiting their innately high sensitivity or responsivity to low intensity, low frequency exogenous electrical currents or by other mechanical, thermal or chemical means.

While increased positive focal or segmental positive pressure or decreased temperature to selectively recruit fibers may be used in most embodiments, negative pressure (e.g., partial or complete vacuum) or increased temperature may be also utilized. All means to selectively recruit nerve fibers may be applied to neural structures, so long as care is exercised to protect their integrity.

While delivery of electrical currents may be the preferred stimuli for activation of recruited fibers, chemical, mechanical, thermal and optical/photonic stimuli may be also used in any combination.

Turning to FIG. 1A, a medical device system 100 according to one embodiment of the present disclosure is schematically depicted. The medical device system 100 may comprise an electrode 110 coupled to a first location of a nerve 105. The electrode 110 may be capable of applying an electrical signal to the first location of the nerve 105.

The nerve 105 may be any anatomical neural structure, such as a cranial nerve, a peripheral nerve, or a spinal root. In one embodiment, the nerve is a vagus nerve (cranial nerve X). Generally, the nerve 105 will comprise one or more fiber types, which may include myelinated and unmyelinated fibers. For many nerves, and especially for cranial nerves, the myelinated fibers include A-fibers and B-fibers, and the unmyelinated fibers include C-fibers.

The electrode 110 may be selected from any electrode known in the art for use in electrically stimulating nerves, including cranial nerves, peripheral nerves, or spinal roots. In a particular embodiment, the electrode 110 may be a helical circumneural electrode, such as the electrodes incorporated into the PerenniaFlex lead/electrode system, produced by Cyberonics, Inc., Houston, Tex. The electrode 110 may be configured to deliver an electrical stimulation therapy to the nerve 105 (e.g., a vagus nerve) treat a medical condition, such as epilepsy, depression, or a cardiovascular disorder. Other electrodes known in the art, such as cuff electrodes, paddle electrodes, needle electrodes, wire electrodes, etc., may be used in addition to or instead of helical electrodes. Electrodes may be placed on the epineurium or beneath it (e.g., in the perineurium and/or endoneurium or in the structures contained within these membranes (intrafascicular electrodes).

The medical device system 100 may also comprise a nerve pressure delivery device (NPD) 120, such as a pressure delivery cuff as shown in FIG. 1A, coupled to a second location of the nerve 105. NPD 120 may be capable of applying a first pressure to the second location of the nerve 105. In one embodiment, NPD 120 may be capable of applying a plurality of pressures to the second location. In one embodiment, NPD 120 may comprise a clamp or other device that continuously applies a first pressure to the nerve. However, such an embodiment is not preferred because it may provide an elevated risk of damage to the nerve or may alter the overall function of the nerve by permanently changing the function of one or more nerve fiber types.

In one embodiment, NPD 120 may be capable of providing a variable range of pressures to the nerve 105, which may include any pressure up to a maximum pressure that may be safely applied to the nerve without causing damage.

In some embodiments, NPD 120 may be capable of providing a continuously variable pressure, while in other embodiments it may be capable of providing one or more programmed pressures to the second location. In one embodiment, pressure is provided to the nerve only in close temporal proximity to an electrical signal that is applied to the nerve; otherwise, pressure is not applied to the nerve.

In one embodiment, NPD 120 may be capable of providing a first pressure to a second location of the nerve 105 for a blocking time period, during which one or more of the activation threshold and/or conduction thresholds for at least one nerve fiber type in the nerve 105 is altered. NPD 120 may be capable of not providing pressure to the nerve during a non-blocking time period. In a particular embodiment, NPD 120 may provide a first pressure to the second location of nerve 105 while an electrical signal is applied to the nerve at the first location, and not provide a pressure to nerve 105 when the electrical signal is not applied to the nerve. Such an approach may minimize the risk of mechanically induced damage to, or altered function of, nerve 105. In one embodiment, the manner and modes by which pressure is applied to nerve 105 by NPD 120 may be programmed by a user from a programming device. NPD 120 may apply positive or negative pressure to nerve 105.

In some embodiments, electrode 110 and NPD 120 may comprise separate devices at different first and second locations, as shown in FIG. 1A. In one embodiment (not shown in FIG. 1A), electrode 110 and NPD 120 may be part of an integrated device including both an electrode 110 and an NPD 120, and capable of applying both an electrical signal and a pressure to a single physical location on the nerve that comprises both the first and second locations.

Referring again to FIG. 1A, pressure may be applied to the nerve 105 from NPD 120 in a number of different ways, such as by pumping a fluid (e.g., a gas or a liquid) into a cuff as shown in FIG. 1A, by altering the temperature of a shape memory material (e.g., heating or cooling a circumneural nitinol ring), by applying an electrical current to a piezoelectric material, by use of a spring element, or by use of a worm gear to drive a clamp mechanism, among other techniques.

Although FIG. 1A depicts NPD 120 as being circumneural, in other embodiments, NPD 120 may be configured for deployment in other orientations relative to the second location of the nerve 105. In one embodiment, NPD 120 may be C-shaped or cover only a portion of the periphery of the nerve. In another embodiment, NPD 120 may be intraneurally (intra-fascicular) placed.

The first location (to which the electrode 110 is coupled) and the second location (to which NPD 120 is coupled) may be in any orientation. However, in embodiments in which electrode 110 and NPD 120 comprise separate structural elements (as shown in FIG. 1A), the selective blocking of action potential conduction provided by operation of NPD 120 is only effective with regard to action potentials propagating from electrode 110 in the direction of NPD 120. Therefore, if the electrical signal applied at 110 is applied as a therapy for a condition in the brain (e.g., epilepsy), NPD 120 should be proximal to the brain relative to electrode 110. Similarly, if the electrical signal applied at 110 is applied as a therapy for heart disease (e.g., congestive heart failure), or to block vagal nerve impulses traveling for example towards the heart, NPD 120 should be proximal to this organ relative to electrode 110. More generally, for an end-target organ or body structure for which selective recruitment of action potentials is desired, NPD 120 should be proximal to the organ relative to electrode 110. For embodiments having a unitary electrode and NPD acting at a single physical location on the nerve, the selective recruitment may be effected by altering only the activation threshold of the target nerve type(s), since the issue of conduction does not apply.

Referring again to FIG. 1A, the medical device system 100 may also comprise a medical device 130 operatively coupled to the electrode 110 and NPD 120. The medical device 130 may be configured to direct NPD 120 to apply a first pressure to the second location of nerve 105. In one embodiment, the first pressure is sufficient to substantially modify activation or conduction thresholds on at least one of an A-fiber population or B-fiber population of the nerve at the second location for a blocking time period. Medical device 130 may also be configured to direct the electrode 110 to apply an electrical signal to the first location of the nerve 105 during the blocking time period. In one embodiment, the medical device 130 may be configured to direct the NPD 120 to cease applying the first pressure to the second location after the blocking time period has elapsed. This may be done to avoid damage to the nerve that may be associated with applying pressure to the nerve for extended time periods. More than one NPD 120 may be placed in the same nerve as needed for the clinical application at hand.

Figure 1B:
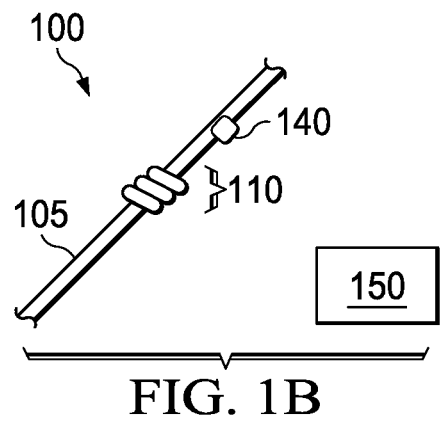
FIG. 1B provides a stylized diagram of another medical device system implanted into a patient's body, in accordance with one illustrative embodiment of the present disclosure.

Turning to FIG. 1B, another embodiment of a medical device system 100 is depicted. Many elements of FIG. 1B are the same as in FIG. 1A, including nerve 105 and electrode 110, and will not be discussed further. The medical device system 100 may comprise a thermal manipulation unit (TMU) 140 coupled to a second location of the nerve 105 capable of heating or cooling the second location of the nerve 105. The TMU 140 may be a Peltier device, or one capable or circulating a coolant/refrigerant or a heating fluid, among other heating and cooling apparatus and techniques. Heating or cooling of the nerve using TMU 140 may be controlled by a medical device 150 to prevent exposure of nerve 105 to temperatures that may damage it or alter its function for periods of times longer than those required for blockage of conduction of impulses along certain fiber types. The duration of cooling or heating will also controlled to minimize risk of nerve damage or prolonged (for the task at hand) dysfunction. Safety limits may be set to minimize one or both of the temperature to which the second location of the nerve may be heated or cooled, as well as the time of such heating or cooling.

In one embodiment, TMU 140 may heat or cool only a portion of the periphery of the nerve, as shown in FIG. 1B. In other embodiments, TMU 140 may be completely circumneural, or may involve a plurality of independently operable elements to heat and cool particular portions of the periphery of the nerve. The TMU 140 may be endowed with probes that may be safely placed inside a nerve to cool down or heat up certain fiber bundles or fascicles.

Regardless of the particular configuration of TMU 140, medical device 150 may be configured to direct the thermal manipulation unit 140 to heat and/or cool the second location of nerve 105, wherein the heating and/or cooling is sufficient to substantially modify activation and/or conduction threshold(s) on at least one fiber population at the second location of nerve 105 for a blocking time period.

In one embodiment, cooling the nerve 105 at the second location may substantially modify conduction of an A-fiber population or B-fiber population for a blocking time period. Medical device 150 may further be configured to direct electrode 110 to apply an electrical signal to the first location of the nerve 105 during the blocking time period.

Without being bound by theory, cooling a nerve comprising A-, B-, and C-fibers may be employed at a second location using TMU 140 to reduce the ability of A-fibers, or both A- and B-fibers to conduct action potentials at the second location. Therefore, if an electrical signal is applied to a first location of nerve 105 using electrode 110, wherein the electrical signal is sufficient to induce action potentials in A-, B-, and C-fibers, conduction of such action potentials on the A-fibers or the A- and B-fibers may be blocked at the second location of the nerve, while conduction of such action potentials on B- and C-fibers, or C-fibers alone, may proceed through the cooled portion of the nerve. In other words, the medical device system 100 may be used to selectively recruit C-fibers or B- and C-fibers in the nerve.

Without being bound by theory, heating a nerve 105 comprising A-, B-, and C-fibers may be employed at a second location using TMU 140 to reduce the ability of C-fibers, or both B- and C-fibers, to conduct action potentials through the heated portion of the nerve. In other words, TMU 140 may be used to selectively recruit A-fibers or A- and B-fibers in the nerve by heating at least a portion of the nerve at the second location. Although A- and/or B-fibers may also be selective recruited by applying an electrical signal of low energy to the nerve, with the electrical current being below the activation threshold of C-fibers or B- and C-fibers but above that of A-fibers or A- and B-fibers, using heat to block conduction on C-fibers or B- and C-fibers allows the application of higher energy electrical signals to selectively recruit more A-fibers or A- and B-fibers than is possible at lower current intensities.

In some embodiments, the medical device system may comprise a plurality of NPDs 120 and/or TMUs 140. For example, the medical device system may comprise two NPDs 120 or two TMUs 140. In such embodiments, the two or more NPDs 120 and/or TMUs 140 may be located in positions flanking the electrode 110, such that at least one NPD 120*p* and/or TMU 140*p* is proximal to the brain relative to electrode 110, and at least one other NPD 120*d* and/or TMU 140*d* is distal to the brain relative to electrode 110. In such embodiments, activation or conduction may be differentially blocked in the afferent (toward the brain) and efferent (away from the brain) directions. For example, an electrical signal delivered via electrode 110 to a nerve 105 in the neck of a patient may activate all of A-, B-, and C-fibers. However, it may be desirable to block efferent conduction in the direction of the heart on some or all of A-, B-, or C-fibers to minimize a reduction of heart rate that might occur if efferent conduction on all fibers were not blocked. In the afferent detection, however, it may be desirable to block conduction in the direction of the brain on a different set of some or all of A-, B-, or C-fibers to produce a desired effect in the brain.

For another example, delivery of an electrical signal by electrode 110 to a point on the vagus nerve that is proximal to the brain relative to the recurring laryngeal nerve (a branch of the vagus nerve) may induce action potentials that propagate efferently down the recurring laryngeal nerve. Because the recurring laryngeal nerve innervates the vocal cords and related anatomical structures, these induced action potentials may reversibly impair operation of the voice, leading to a husky or whispery voice while the electrical signal is being delivered to the vagus nerve. Therefore, it may be desirable to use an NPD 120*d* and/or a TMU 140*d* to block substantially all efferent conduction from the site of electrode 110, thereby reducing any impairment of the voice. At the same time, it may be desirable to use an NPD 120*p* and/or a TMU 140*p* to block substantially all afferent conduction on one of more fiber types (e.g., A- and B-fibers) from the site of electrode 110, thereby allowing selective recruitment of the unblocked fiber type(s) (e.g., C-fibers) in the afferent direction.

In other embodiments, the medical device system may comprise a single NPD 120 or TMU 140, such that activation or conduction of electrical signals at or through the location of the NPD 120 or TMU 140 is differentially allowed depending on the direction of electrical signal propagation. For example, it may be desirable at some times to block efferent conduction on some or all of A-, B-, or C-fibers of endogenous signals (generated by the brain) and/or signals delivered to the nerve 105 by an electrode 110*p*. It may also be desirable at different times to block afferent conduction on a different set of some or all of A-, B-, or C-fibers of endogenous signals (generated by the viscera) and/or signals delivered to the nerve 105 by an electrode 110*d*.

In some embodiments, one or more NPDs 120 and/or TMUs 140 may be used to reversibly block all conduction or activation of action potentials in both the afferent and efferent direction. Such a blocking is comparable to a vagotomy (surgical severance of the vagus nerve), but with the advantage that such blocking is reversible when implemented by NPDs 120 and/or TMUs 140, in contrast with surgical blocking, which is irreversible. In yet another embodiment. the NPD 120 and TMU 140 may be placed side by side proximally or distally to the brain or heart. In another embodiment, the NPD 120 and TMU 140 may integrated into a single unit/device.

Figure 2A:
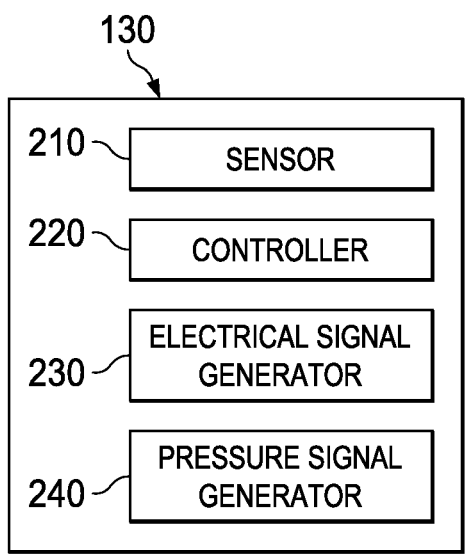
FIG. 2A provides a block diagram of a medical device, in accordance with one illustrative embodiment of the present disclosure.

FIG. 2A presents a block diagram of a medical device 130 as shown in FIG. 1A. Medical device 130 may comprise a sensor 210 to receive at least one physiological data stream. The physiological data stream(s) may comprise autonomic data, such as cardiac data (e.g., heart rate, heart rate variability), respiratory data (e.g., breathing rate, tidal volume), skin resistivity, muscle activity, or eye movement, among others. Alternatively or in addition, the physiological data stream may comprise neurologic data, such as body movement data, responsiveness data, awareness data, EEG or ECoG, among others. The physiological data stream may comprise other types of physiological data. More information regarding physiological data streams and sensors suitable to receive them is provided by U.S. patent application Ser. No. 12/896,525, filed Oct. 1, 2010, which is incorporated herein by reference. Although not depicted in FIG. 2A, medical device 130 may also comprise hardware and/or software for conditioning and processing the physiological data stream(s), e.g., sense-amps, pre-filters, filters, A/D and/or D/A converters, memory, etc.

Medical device 130 may also comprise a controller 220 to direct operations of one or more other units of medical device 130 or medical device system 100. In one embodiment, the controller 220 may determine a type and/or parameters of the electrical signal to be applied to the first location of the nerve 105. The parameters of the electrical signal may include pulse amplitude, frequency, pulse width, on-time, off-time, waveform shape, inter-stimulus interval which may be uniform or variable, duty cycle, the timing of signal application, or two or more thereof, among others, and may be stored in a memory of the device (not shown).

Controller 220 may further control one or more pressures to be applied through the NPD 120 to the nerve 105. The controller 220 may control the magnitude of the pressure, the duration of the pressure, and the time at which the pressure is applied, and changes (including rates of change) in the pressure applied to the nerve 105 through NPD 120. In this manner, controller 220 may be used to substantially block action potential activation and/or conduction on A-fibers alone, on A- and B-fibers, or on all of A-, B-, and C-fibers. In some embodiments, the controller 220 may select which fiber type(s) to selectively recruit, based on information received from sensor 210 and/or other sources (a device memory (not shown), an input from a patient, caregiver, or physician, etc.).

Medical device 130 may also comprise an electrical signal generator 230 configured to apply an electrical signal to the first location of the nerve 105 using electrode 110. In some embodiments, one or more parameters of the electrical signal from electrical signal generator 230 may be based upon the physiological data stream sensed by sensor 210.

Medical device 130 may also comprise a pressure signal generator 240 configured to apply the first pressure to the second location of the nerve 105 using NPD 120 to substantially block conduction on at least one of an A-fiber population or a B-fiber population of the second location of the nerve.

FIG. 2B presents a block diagram of the medical device 150 as shown in FIG. 1B. Medical device 150 may comprise a sensor 210, controller 220, and electrical signal generator 230, generally as described above with reference to FIG. 2A. In some embodiments wherein the medical device system 100 comprises both a cooling unit and a heating unit, the controller 220 may determine a fiber-type population of the portion of the nerve 105 for selective recruitment, based on data received from body sensors or from a user.

Medical device 150 may also comprise a cooling unit 250 configured to cool the second location of the nerve using TMU 140 to substantially block conduction on at least one of a A-fiber population or a B-fiber population at the second location of the nerve 105. The cooling unit 250 may be configured to cool the second location by issuing instructions to TMU 140. Medical device 150 may also comprise a heating unit 260 configured to heat the second location of the nerve using TMU 140 to substantially block conduction on at least one of a B-fiber population or a C-fiber population of the second location of the nerve. The heating unit 260 may be configured to heat nerve 105 by issuing instructions to TMU 140.

FIG. 3 presents a flowchart depiction of a method according to one embodiment of the present disclosure. In the method, a nerve fiber type within a nerve, such as a cranial nerve or a peripheral nerve, may be selectively recruited by receiving at 310 a prompt to apply an electrical signal to a first location of the nerve. The prompt may be issued by hardware, software, and/or firmware in a medical device system 100; by a patient, a caregiver, or a medical professional; or by another source, and may be received by appropriate hardware, software, and/or firmware in a medical device system 100.

The method may further comprise applying at 320 a first pressure to a second location of the nerve, wherein the pressure is sufficient to substantially block activation and/or conduction on at least one of an A-fiber population or a B-fiber population through the second location of the nerve for a blocking time period.

In addition, the method may further comprise applying at 330 an electrical signal to the first location during the blocking time period. In some embodiments, application of the first pressure to the second location may be discontinued after the application of the electrical signal.

FIG. 4 presents a flowchart depiction of a method according to another embodiment of the present disclosure. In this method, receiving a prompt at 410 and applying an electrical signal at 430 may be as described above with reference to steps 310 and 330 in FIG. 3.

The method depicted in FIG. 4 may further comprise cooling the nerve at a second location of the nerve at 420, wherein the cooling is sufficient to substantially block activation and/or conduction on at least one of an A-fiber population or a B-fiber population at the second location for a blocking time period.

Although the use of pressure and the use of thermal manipulation have been separately described as techniques of blocking action potential conduction in particular fiber types of nerves, they may be used together. In other words, a medical device system 100 may comprise both a NPD 120 and a TMU 140, with appropriate controlling hardware, software, and/or firmware for the use of both, and the methods depicted in FIGS. 3 and 4 may be performed simultaneously or contemporaneously.

In a further embodiment, receiving a prompt to selectively recruit a nerve fiber type within a nerve 105 may be implemented using a neurogram to measure compound action potentials on the nerve. Pressures and/or temperatures (or heating/cooling rates) at which selective nerve fiber types are blocked within the nerve may be determined manually or by an automated program that incrementally changes one or both of pressure and temperature provided by NPD 120 and TMU 140. This may be done, e.g., by applying a particular pressure and/or temperature (or heating/cooling rate) to the nerve, applying an electrical signal to the nerve during application of the pressure/temperature, and measuring the compound action potential of the nerve induced by the electrical signal. The compound action potential may be analyzed to determine A-fiber, B-fiber, and C-fiber components, and the results may be compared to other neurograms in which no blocking pressure/temperature is applied to the nerve to determine which fiber types have been blocked, and the magnitude of the blocking effect. The pressure, thermal or chemical (dose/concentration) parameters required for blockage may then be stored in memory for later use (e.g., by a physician). Since nerve fiber excitability is non-stationary (i.e., it is multi-factorially determined and the factors vary as a function of time or state), the effective parameters for blocking may also vary. Differences in blocking parameters, if any, for a variety of electrical signals may be stored in memory with all relevant temporal (e.g., time of day) and the state information. The data necessary for pressure and/or thermal blockage of certain fiber types for each of a number of different electrical signals may be stored in, e.g., a lookup table for use by a medical device to achieve a desired level of blockage. An automated program may be employed to periodically regenerate the data as the patient's condition changes.

Adjustments to blocking pressure and/or temperatures may be implemented automatically or manually, either using the stored neurogram settings or actual (real-time) neurogram information recorded during electrical stimulation. In addition to adjustments made to the pressure and/or temperature settings made from neurogram information, adjustments to these values may also be made from therapeutic efficacy determinations or adverse event determinations from sensed body data (e.g., heart rate, skin resistivity, respiratory rate, tidal volume, blood pressure, EEG, ECoG, cognitive data, kinetic data, etc.) after the recruited nerve fibers are activated using electrical or some other stimulation modality (e.g., chemical). More generally, pressure and/or temperature/heating/cooling and/or electrical settings may be adjusted or optimized based on therapeutic efficacy or adverse events.

The foregoing process for identifying pressure, temperature or chemical settings to achieve particular fiber recruitment levels may be automated. In particular, a program may be implemented in which appropriate pressure and temperature settings, are determined based upon the output of the neurogram. The pressures, temperatures and chemicals (type and dose/concentration) at which selective fiber types are blocked to a desired level may be identified and then stored memory. In one embodiment, electrical stimulation may be enabled only when the effective (for the task at hand) blocking pressures, temperatures and/or dose/concentration of chemicals are reached. Adjustments to pressure, temperature and type of chemical, concentration/dose may be made in real-time using the neurogram or other measured effects of the therapy. Blocking pressures, temperatures or concentration/dose may be determined based on the therapeutic efficacy, or by the presence of adverse effects caused by said blocking modalities. The effect of selective activation of fibers may be determined based on autonomic, neurologic, metabolic or other signals, and used to determine the optimal temperature, pressure or type of chemical and concentration applied to a nerve. As used herein, "optimal" or "optimized" may refer to parameters providing an improvement in response relative to other outcomes.

Figure 5:
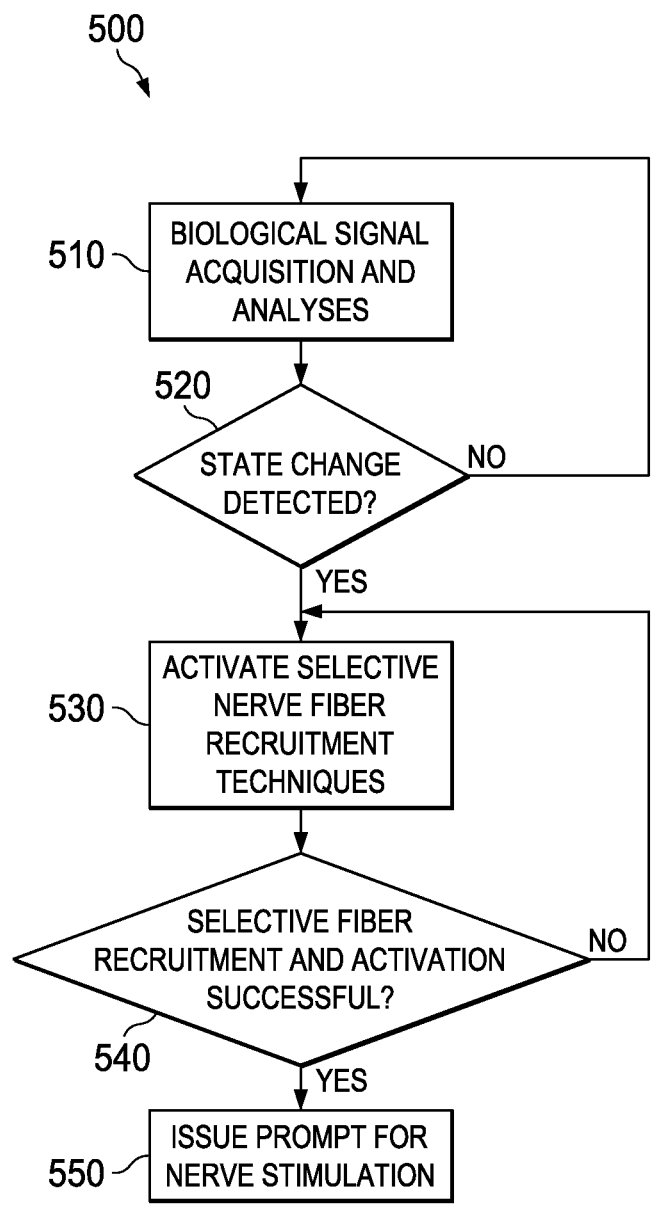
FIG. 5 provides a flowchart of a method for selectively recruiting and/or activating a fiber type, in accordance with one illustrative embodiment of the present disclosure.

Turning to FIG. 5, a flowchart depiction of a method 500 according to some embodiments of the present disclosure is shown. Method 500 comprises acquiring and analyzing at 510 at least one biological signal. The analysis at 510 may reveal a state change in one or more tissues, organs, or organ systems of a patient, e.g., an epileptic event in the brain of a patient, among other possibilities. If a state change is not detected at 520, flow returns to acquiring and analyzing at 510. If a state change is detected at 520, the method may comprise selectively recruiting at 530 one or more nerve fiber populations in a nerve of interest, such as a cranial nerve, a peripheral nerve, or a spinal root. Selective recruiting at 530 may allow later stimulation of a desired nerve fiber population to prevent, abort, or minimize the intensity of, i.e., treat, the state change. The biological signals may be neurological (cognitive, kinetic, EEG, ECOG, chemical, thermal, mechanical), autonomic (EKG, blood pressure, respirations, skin resistance; catecholamine concentrations or their metabolites), endocrine (cortisol, prolactine) metabolic (pH, glucose) or markers of tissue stress (lactic acid, CK, free radicals etc.). More information on such signals and their detection may be found in U.S. Pat. No. 8,337,404, issued Dec. 25, 2012; U.S. patent application Ser. No. 13/098,262, filed Apr. 29, 2011; and U.S. patent application Ser. No. 13/288,886, filed Nov. 3, 2011; all of which are hereby incorporated herein by reference.

After selectively recruiting at 530, a determination at 540 may be made as to whether the selective recruiting at 530 was successful. This determination at 540 may be based on a neurogram, on evoked responses recorded from the brain or on changes in cortical rhythms. If no, selectively recruiting at 530 may be continued or modified. If selective recruiting at 530 was determined at 540 to be successful, a prompt may be issued at 550 for nerve stimulation of the selectively recruited fiber population. Such stimulation of a desired nerve fiber population may prevent, abort, or minimize the intensity of, i.e., treat, the state change.

FIGS. 6-9 generally show the effect of pressure or temperature modulation on blockage of activation or conduction on one or more fiber populations within a nerve. FIGS. 6-9 are taken from previously published papers.

Figure 6A:
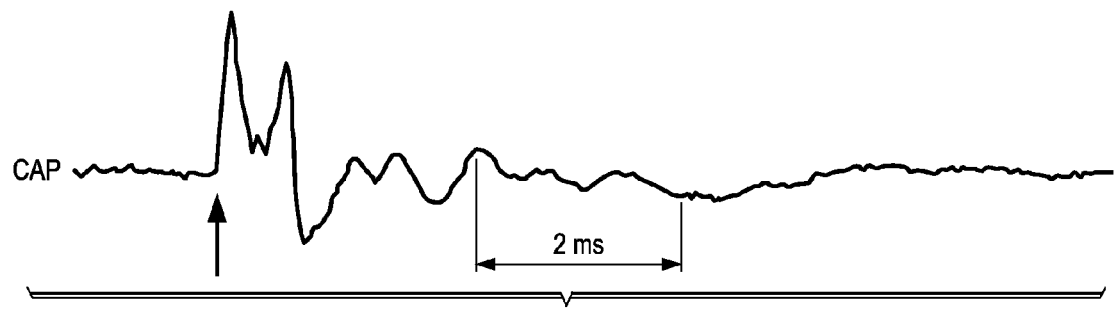
FIG. 6A shows an example of vagus nerve compound action potential (CAP) showing A fiber action potentials, in accordance with one illustrative embodiment of the present disclosure.

FIG. 6A shows an example of vagus nerve compound action potential (CAP) showing A fiber action potentials. Specifically, an electrical stimulus is delivered to a vagus nerve at the point indicated by the upward arrow. The amplitude of the stimulus was chosen to induce action potentials on A fibers with minimal activation of other fiber types, i.e., the amplitude was greater than ATA and less than ATB. The local peak immediately after delivery of the stimulus is an artifact of stimulus. The next largest peak, about 0.75 msec after delivery of the stimulus, is an action potential propagated along A fibers. The shorter humps seen about 1.5-5 msec after delivery of the stimulus are action potentials propagated along B fibers.

Figure 6B:
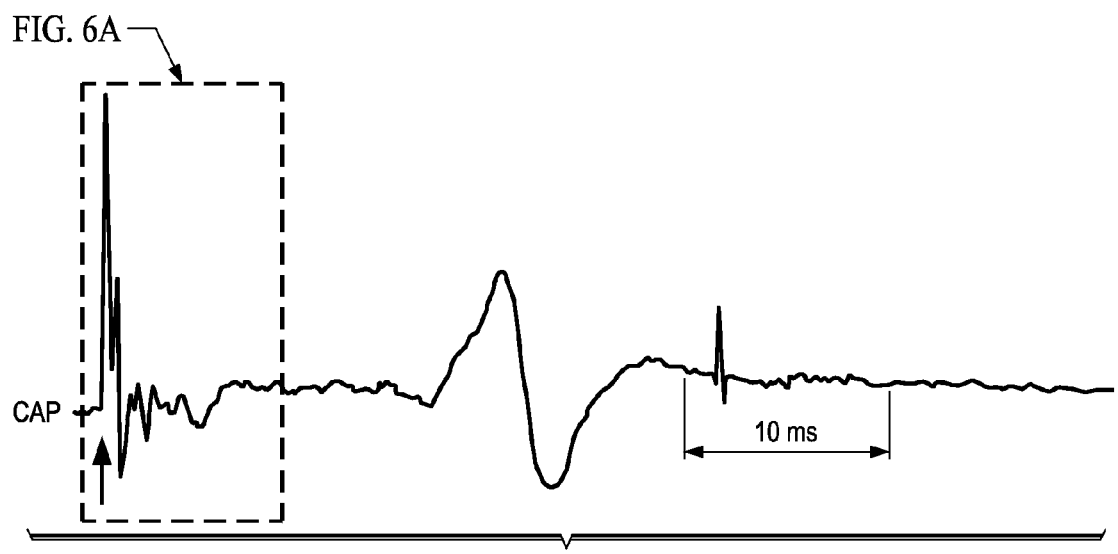
FIG. 6B shows an example of vagus nerve compound action potential (CAP) showing A, B, and C fiber action potentials, on a longer timescale than that shown in FIG. 6A, in accordance with one illustrative embodiment of the present disclosure.

FIG. 6B shows an example of vagus nerve compound action potential (CAP) showing A, B, and C fibers, on a longer timescale than that shown in FIG. 6A. The delivered electrical stimulus had an amplitude sufficient to activate all three fiber types, i.e., the amplitude was greater than ATC. By expanding the scale, action potentials propagated along C fibers can be clearly seen in the wide peak around 18 msec after delivery of the stimulus.

In both FIGS. 6A and 6B, activation and conduction on all fiber types were unblocked by pressure, temperature, or other means.

Figure 6C:
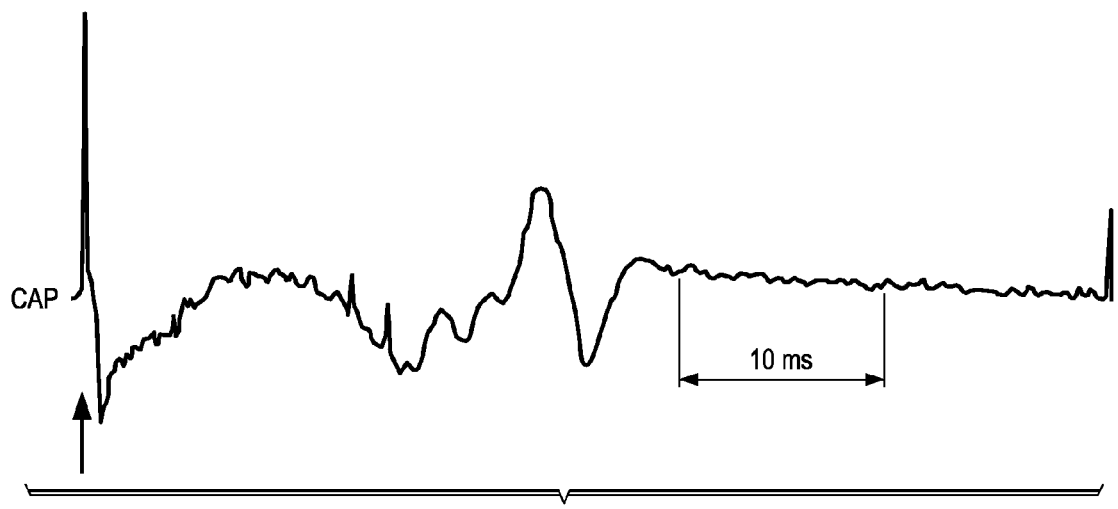
FIG. 6C shows an example of blocking of activation/conduction on A fibers of a vagus nerve, in accordance with one illustrative embodiment of the present disclosure.

FIG. 6C shows an example of blocking of activation/conduction on A and B fibers of a vagus nerve by cooling. Cooling was sufficient to block activation/conduction on A fibers (compare the first few msec after delivery of the stimulus in this figure with FIG. 6B), while activation/conduction on C fibers was unimpaired.

Figure 6D:
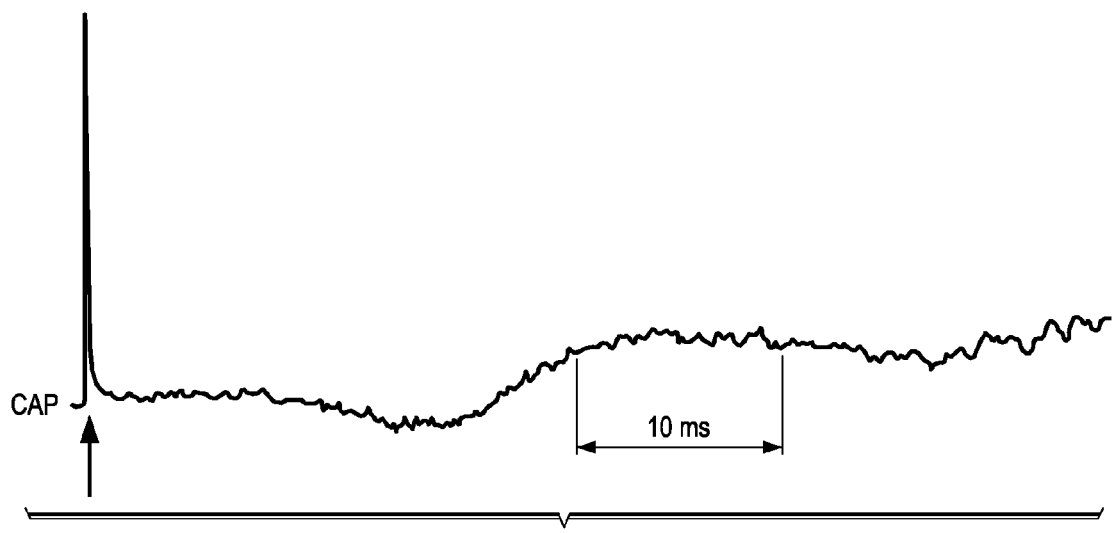
FIG. 6D shows an example of blocking of activation/conduction on A, B, and C fibers of a vagus nerve, in accordance with one illustrative embodiment of the present disclosure.

FIG. 6D shows an example of blocking of activation/conduction on A, B, and C fibers of a vagus nerve. In contrast to FIG. 6C, cooling was sufficient to block activation/conduction on all fiber types. As a result, only the peak for the stimulation artifact is visible. No fiber types were activated or conducted action potentials during roughly 50 msec after stimulation delivery.

Figure 7:
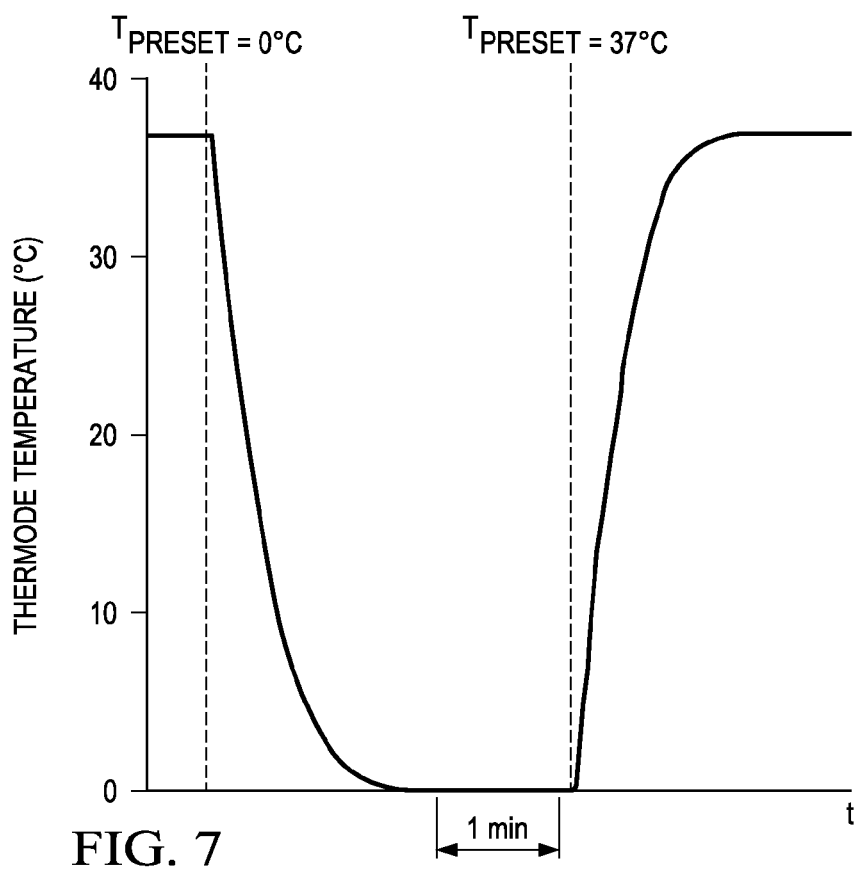
FIG. 7 shows step responses of the temperature of a cervical vagus nerve in a rabbit in response to in vivo local nerve cooling, in accordance with one illustrative embodiment of the present disclosure.

FIG. 7 shows step responses of the temperature of a cervical vagus nerve in a rabbit in response to in vivo local nerve cooling. As can be seen, application of cooling to 0° C. (first vertical dashed line) cooled the nerve from body temperature to 0° C. within about 2 min. Thereafter, heating to 37° C. warmed the nerve from 0° C. to body temperature within about 90 sec.

Figure 8:
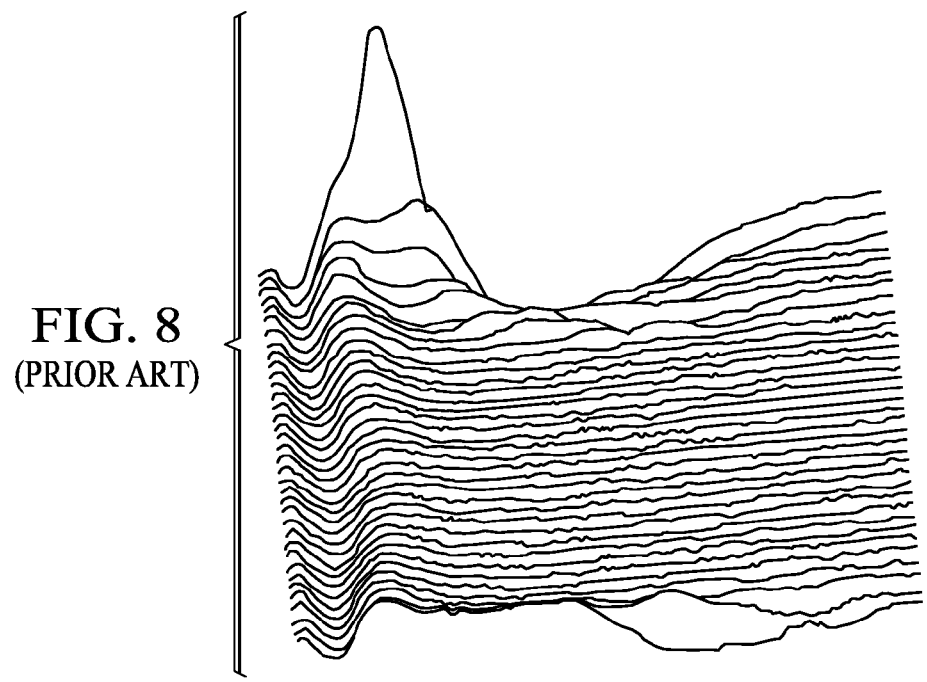
FIG. 8 shows an example of conduction blocking of A fibers in a rabbit vagus nerve in response to local nerve cooling, in accordance with one illustrative embodiment of the present disclosure.

FIG. 8 shows an example of rapid conduction blocking of A fibers in a rabbit vagus nerve in response to local nerve cooling. FIGS. 7-8 are taken from Patberg, et al., J. Neurosci. Methods, 10:267-275 (1984).

Figure 9:
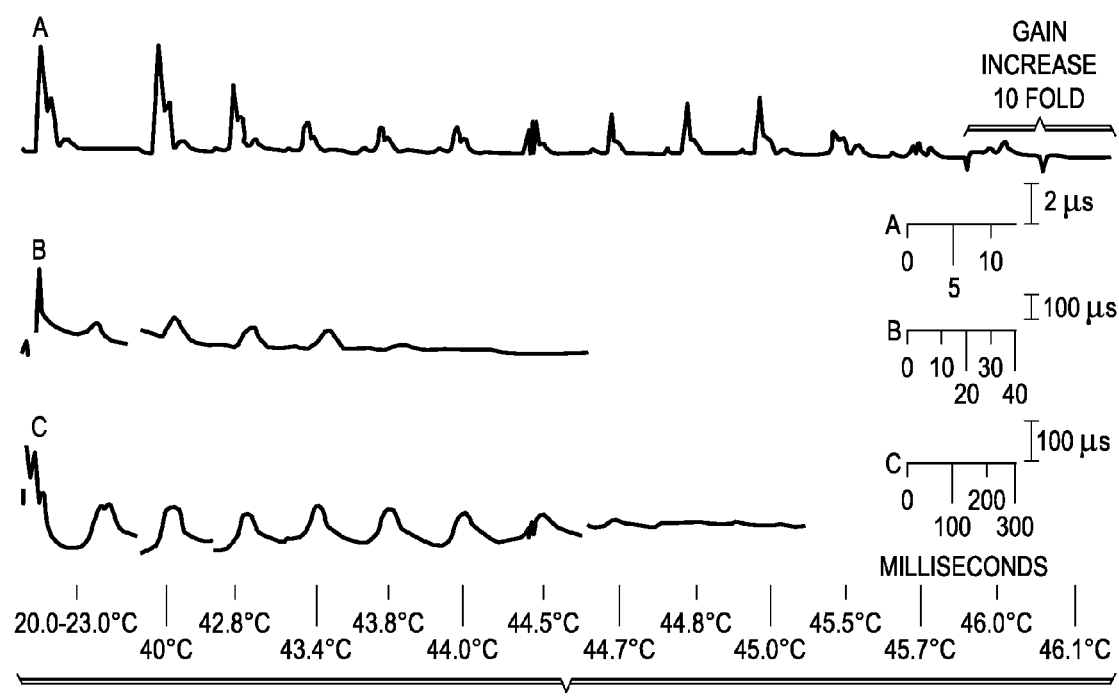
FIG. 9 shows an effect of local heating on conduction in A, B, and C fibers in bullfrog sciatic nerves, in accordance with one illustrative embodiment of the present disclosure.

FIG. 9 shows an effect of local heating on conduction in A, B, and C fibers in bullfrog sciatic nerves. As can be seen, heating to about 42.8° C. reduced the amplitude of conducted action potentials in A fibers by about 50%, with further reduction observed for heating to about 43.4° C. B fibers were the most sensitive to heating, decreasing in amplitude by about 80% before the temperature reached 30° C. and disappearing just below 44.0° C. The C fibers were least sensitive to heating, not reaching a minimum amplitude until heated to about 44.8° C. FIG. 9 is taken from Treanor, et al., Am. J. Physiol. 175:258-262 (1953).

Additional embodiments of the disclosure are described herein in the following numbered paragraphs.

100. A medical device system for selectively activating a nerve fiber population type, comprising:

an electrode coupled to a first location of a nerve, said electrode capable of applying an electrical signal to said first location;

a pressure delivery device coupled to a second location of said nerve capable of applying a first pressure to said second location of said nerve; and a medical device operatively coupled to said electrode and said pressure delivery device, said medical device capable of:

directing said pressure delivery device to apply a first pressure at said second location of said nerve, said pressure sufficient to substantially modify at least one of electrical activation and electrical conduction of at least one of an A-fiber population or B-fiber population at said second location for a blocking time period; and directing said electrode to apply said electrical signal to said first location of said nerve during said blocking time period.

101. The medical device of numbered paragraph 100, wherein said medical device comprises a controller configured to select a fiber-type population of said portion of the cranial or peripheral nerve whose electrical activation or electrical conduction is modified by said pressure delivery device.

102. The medical device system of numbered paragraph 100, wherein said pressure delivery device is intrafascicular and has an adjustable circumference.

103. A medical device system for selectively stimulating a nerve fiber, comprising:

an electrode coupled to a first location of a nerve, said electrode capable of applying an electrical signal to said first location;

a thermal manipulation unit coupled to a second location of said nerve, capable of heating or cooling said nerve at said second location; and a medical device operatively coupled to said electrode and said thermal manipulation unit, said medical device comprising:

a controller an electrical signal generator to apply an electrical signal to the first location of said nerve using said electrode; and a thermal manipulation signal generator to heat or cool said nerve at said second location using said thermal manipulation unit, to substantially block at least one of activation or conduction in at least one of an A-fiber population, a B-fiber population, or a C-fiber population of said second location of said nerve.

104. The medical device system of numbered paragraph 103, wherein the heating or cooling of the nerve is performed using a cooling or a heating element placed on the epineurium.

105. The medical device system of numbered paragraph 103, wherein the cooling or heating element is intra-neural/intra-fascicular.

106. The medical device system of numbered paragraph 103, further comprising:

a nerve pressure device coupled to a third location of said nerve, capable of applying a first pressure to the third location; and said medical device further comprising a pressure signal generator to apply said first pressure to said third location of said nerve using said nerve pressure device.

107. The medical device system of numbered paragraph 103, wherein at least one parameter defining said electrical signal is programmably selected, said at least one parameter selected from a pulse current, a pulse width, a frequency, an on-time and an off-time.

108. The medical device system of numbered paragraph 103, wherein said thermal manipulation unit is programmably selectable for applying a plurality of temperature values and an on-time and an off-time to said second location of said nerve.

109. The medical device system of numbered paragraph 103, wherein said thermal manipulation unit is a Peltier device to cool or heat.

110. A medical device system for selectively stimulating a nerve fiber, comprising:

an electrode coupled to a first location of a nerve, said electrode capable of applying an electrical signal to said first location;

a thermal manipulation unit coupled to a second location of said nerve, capable of heating or cooling said nerve at said second location;

a nerve pressure device coupled to a third location of said nerve, capable of applying a first pressure to the third location and a medical device operatively coupled to said electrode, to said thermal manipulation unit and to said nerve pressure device, said medical device comprising:

a controller;

an electrical signal generator to apply an electrical signal to the first location of said nerve using said electride;

a thermal manipulation signal generator to heat or cool said nerve at said second location using said thermal manipulation unit; and a nerve pressure device capable of applying pressure at said third location to substantially block at least one of activation or conduction in at least one of an A-fiber population, a B-fiber population, or a C-fiber population of said second location of said nerve.

111. The medical device system of numbered paragraph 110, wherein the second and third locations are the same.

112. A method for selectively recruiting a nerve fiber type within a cranial nerve, a peripheral nerve or a spinal root for treating a patient having one of epilepsy and depression, comprising:

applying an electrical signal to of said nerve, said electrical signal having an effect of activating only an A-fiber population.

What is claimed is:

1. A method for selectively recruiting a nerve fiber type of a cranial nerve, a peripheral nerve or a spinal root, comprising:

performing an operation selected from one of heating or cooling a second location of said cranial nerve, said peripheral nerve or said spinal root, said heating or cooling sufficient to temporarily and substantially block at least one of activation or conduction on at least a first fiber type of said cranial nerve, said peripheral nerve or said spinal root for a blocking time period; and applying an electrical neurostimulation signal to a first location of said cranial nerve, said peripheral nerve or said spinal root during said blocking time period.

2. The method of claim 1 further comprising selecting at least a second fiber type of said cranial nerve, said peripheral nerve or said spinal root for stimulation by said electrical neurostimulation signal, wherein said at least a second fiber type is different from said at least a first fiber type.

3. The method of claim 1, wherein the at least a first fiber type population is selected from an A-fiber population, a B-fiber population, or a C-fiber population.

4. The method of claim 1, wherein said heating or cooling comprises heating or cooling said cranial nerve, said peripheral nerve or said spinal root to a selected temperature at said second location, and wherein said temperature is programmably selectable.

5. The method of claim 1, further comprising applying a first pressure to a third location of said cranial nerve, said peripheral nerve or said spinal root.

6. A medical device system for selectively stimulating a nerve fiber, comprising:
- an electrode configured to be coupled to a first location of a nerve, said electrode capable of applying an electrical signal to said first location;
- a thermal manipulation unit configured to be coupled to a second location of said nerve, capable of heating or cooling said nerve at said second location; and
- a medical device operatively coupled to said electrode and said thermal manipulation unit, said medical device comprising:
- a controller;
- an electrical signal generator to apply an electrical signal to the first location of said nerve using said electrode; and
- a thermal manipulation signal generator to heat or cool said nerve at said second location using said thermal manipulation unit, to temporarily and substantially block at least one of activation or conduction in at least one of an A-fiber population, a B-fiber population, or a C-fiber population of said second location of said nerve.

7. The medical device system of claim 6, wherein the heating or cooling of the nerve is performed using a cooling or a heating element configured to be placed on the epineurium.

8. The medical device system of claim 6, wherein the cooling or heating element is intra-neural/intra-fascicular.

9. The medical device system of claim 6, further comprising:
- a nerve pressure device configured to be coupled to a third location of said nerve, capable of applying a first pressure to the third location; and
- said medical device further comprising a pressure signal generator to apply said first pressure to said third location of said nerve using said nerve pressure device.

10. The medical device system of claim 6, wherein at least one parameter defining said electrical signal is programmably selected, said at least one parameter selected from a pulse current, a pulse width, a frequency, an on-time and an off-time.

11. The medical device system of claim 6, wherein said thermal manipulation unit is programmably selectable for applying a plurality of temperature values and an on-time and an off-time to said second location of said nerve.

* * * * *